United States Patent [19]

Chauvin et al.

[11] Patent Number: 5,780,702
[45] Date of Patent: Jul. 14, 1998

[54] PROCESS FOR DISPLACING THE DOUBLE BOND IN OLEFINS USING A CATALYTIC COMPOSITION BASED ON TRANSITION METAL COMPLEXES

[75] Inventors: Yves Chauvin, Le Pecq, France; Lothar Mussmann, Hanau Wolfgang, Germany; Hélène Olivier, Rueil Malmaison, France

[73] Assignee: Institut Francais du Petrole, France

[21] Appl. No.: 664,561

[22] Filed: Jun. 17, 1996

[30] Foreign Application Priority Data

Jun. 16, 1995 [FR] France ................. 95 07329

[51] Int. Cl.$^6$ .................. C07C 5/23; C07C 5/25
[52] U.S. Cl. ............ 585/664; 585/665; 585/667; 585/669; 585/670; 585/671
[58] Field of Search ................. 585/664, 665, 585/667, 669, 670, 671

[56] References Cited

U.S. PATENT DOCUMENTS

| | | |
|---|---|---|
| 3,565,823 | 2/1971 | Parshall. |
| 3,657,368 | 4/1972 | Parshall. |
| 3,832,391 | 8/1974 | Parshall. |
| 3,855,323 | 12/1974 | Lyons ................. 585/671 |

*Primary Examiner*—Elizabeth D. Wood
*Attorney, Agent, or Firm*—Millen, White, Zelano & Branigan, P.C.

[57] ABSTRACT

A catalytic composition comprises at least one quaternary ammonium and/or phosphonium salt in which the anion is preferably selected from the group formed by tetrafluoroborate, tetrachloroborate, hexafluorophosphate, hexafluoroantimonate, hexafluoroarsenate, trifluorosulphonate, fluorosulphonate, tetrachloroaluminate, dichlorocuprate, and trichlorozincate, and at least one complex of a transition metal from groups 8, 9 and 10, i.e., iron, ruthenium, cobalt, rhodium, iridium, nickel, palladium and platinum, is for the displacement of the double bond in olefins.

21 Claims, No Drawings

PROCESS FOR DISPLACING THE DOUBLE BOND IN OLEFINS USING A CATALYTIC COMPOSITION BASED ON TRANSITION METAL COMPLEXES

Cross Reference to Related Applications

This application filed Jun. 17, 1995 is related to a concurrently filed application entitled "Novel Catalytic Composition Based on Transition Metal Complexes, and a Process for the Hydrogenation of Unsaturated Compounds" Ser. No. 08/664,539 based on French Application No. 95/07328, by Yves Chauvin et al.

BACKGROUND OF THE INVENTION

The object of the present invention is to provide a process for the isomerization, i.e., displacement of the double bond, of olefins using a catalytic composition resulting from the interaction of an organic-inorganic salt which is liquid at the reaction temperature, hereinbelow termed a "molten salt", and a complex of a transition metal from groups 8, 9 and 10.

A very large number of complexes of transition metals from groups 8, 9 and 10 are known which catalyze, by homogeneous catalysis, the displacement of the double bond in olefins and which are soluble in suitable organic solvents or in the reactants and in the isomerization products. Those catalysts are dealt with in an article in "Principles and Application of Organotransition Metal Chemistry", by J. P. Collman, University Science Books, Mill Valley, U.S.A.

U.S. Pat. No. 3,565,823 describes a composition consisting of a dispersion constituted by a compound, in particular of a transition metal in a salt of tin or germanium and a quaternary ammonium or phosphonium ion. U.S. Pat. 3 657 368 describes an olefin hydrogenation process and U.S. Pat. No. 3,919,271 describes a nitrile hydrogenation process, both using the above composition. U.S. Pat. No. 3,832,391 claims an olefin carbonylation process using the same composition.

The compositions described above have the disadvantage of having a relatively high melting point.

SUMMARY OF THE INVENTION

We have now discovered that the complexes of transition metals from groups 8, 9 and 10, in particular ruthenium, rhodium, iridium, palladium and platinum complexes, combined with an organic-inorganic salt which is liquid at low temperatures, can be used to isomerize olefins.

The catalytic composition comprises at least one compound of a transition metal from groups 8, 9 and 10, in particular complexes of ruthenium, rhodium and iridium, and also of nickel, palladium and platinum, and at least one quaternary ammonium and/or phosphonium salt, termed a "molten salt", said composition resulting from at least partial dissolution of a transition metal compound in a "molten salt".

An object of the invention is to provide a process for the isomerization of olefins, in which the olefin or olefins is/are brought into contact with at least one compound of at least one transition metal from groups 8, 9 and 10, in particular ruthenium, rhodium and iridium, also palladium, platinum and nickel, the compound being at least partially dissolved in a "molten salt". The "molten salt" medium is based on an organic cation and an inorganic action. The isomerization products are slightly soluble or insoluble in the catalytic composition.

Upon further study of the specification and appended claims, further objects and advantages of this invention will become apparent to those skilled in the art.

The "molten salts" of the invention have the general formula $Q^+A^-$ where $Q^+$ represents a quaternary ammonium and/or quaternary phosphonium cation and $A^-$ represents any known anion which can form a liquid salt at low temperatures, i.e., below 150° C., advantageously at most 80° C., preferably below 50° C., for example the following ions: tetrafluoroborate, tetrachloroborate, hexafluorophosphate, hexafluoroantiomonate, hexafluoroarsenate, trifluromethylsulphonate, fluorosulphonate, tetrachloroaluminate, dichlorocuprate, and trichlorozincate. Anions selected from the group formed by trichlorocuprate, tetrachlorocuprate, heptachloroaluminate and decachloroaluminate can be added to anions $A^-$, in particular to those cited above. The quaternary ammonium and/or phosphonium ions preferably have the general formulae $NR^1R^2R^3R^{4+}$ and $PR^1R^2R^3R^{4+}$, or have general formulae $R^1R^2N=CR^3R^{4+}$ and $R^1R^2P=CR^3R^{4+}$, where $R^1R^2$, $R^3$ and $R^4$, which may be identical or different, represent hydrogen with the exception of the cation $NH_4^+$, and preferably a single substituent can represent hydrogen, or hydrocarbon residues containing 1 to 12 carbon atoms, for example saturated or unsaturated, cycloalkyl or aromatic, aryl or aralkyl alkyl groups containing 1 to 12 carbon atoms. The ammonium and/or phosphonium ions can also be derived from nitrogen-containing or phosphorous-containing heterocycles containing 1, 2 or 3 nitrogen and/or phosphorous atoms, with the following, general formulae:

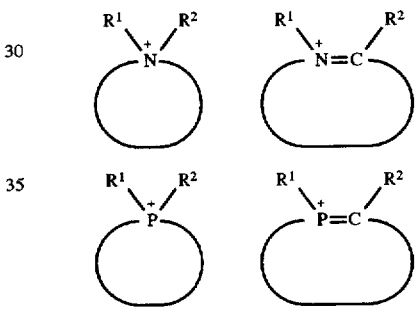

where the cycles are constituted by 4 to 10 atoms preferably 5 to 6 atoms, $R^1$ and $R^2$ being as defined above. The quaternary ammonium or phosphonium cation can also be a cation With formula $R^1R^2N^+=CR^3—R^5—R^3C=N^+R^1R^2$ $R^1R^2P^+=CR^3—R^5—R^3C=P^+R^1R^2$ where $R^1$, $R^2$ and $R^3$, which may be identical or different, are as defined above and $R^5$ represents an alkylene or phenylene residue. Examples of $R^1$, $R^2$, $R^3$ and $R^4$ groups are methyl, ethyl, propyl, isopropyl, butyl, secondary butyl, tertiary butyl, amyl, methylene, ethylidene, phenyl or benzyl radicals; $R^5$ may be a methylene, ethylene, propylene or phenylene group. The ammonium and/or phosphonium cation is preferably selected from the group formed by N-butylpyridinium, N-ethylpyridinium, 3-butyl-1-methylimidazolium, diethylpyrazolium, 3-ethyl-1-methylimidazolium, pyridinium, trimethylphenylammonium, 3-ethyl-1-methylimidazolium, and tetrabutylphosphonium. Examples of suitable salts are N-butylpyridinium hexafluorophosphate, N-ethylpyridiniunm tetrafluoroborate, tetrabutylphosphonium tetrafluoroborate, 3-butyl-1-methylimidazolium hexafluoroantimonate, 3-butyl-1-methylimidazolium hexafluorophosphate 3-butyl-1-methylimidazolium trifluoromethylsulphonate, pyridinium fluorosulphonate, trimethylphenylammonium hexafluorophosphate 3-butyl-1-methylimidazolium tetrachloroaluminate, 3-butyl-1-methylimidazolium heptachloroaluminate, trimethylphenylammonium chloride, 3-etlyl-1-methylimidazolium chloride, tetrabutylphosphonium bromide, N-butylpyridinium chloride, N-ethylpyridinium bromide, 3-butyl-1-methylimidazolium chloride, diethylpyrazolium chloride, and pyridinium hydrochloride. These salts can be used alone or as a milxture. They act as a solvent.

The transition metal compounds for use in accordance with the invention are in general all those transition metal complexes which are known to the skilled person. The are zero-, mono-, di- or trivalent compounds in which the metal is selected from the group formed by Fe, Ru, Os, Co, Rh, Ir, Ni, Pd, Pt, preferably Ru, Rh and Ir, and can for example be bonded to halide, hexafluorophosphate, hexafluoroarsenate, tetrafluoroborate, tetrachloroborate, etc. . . ions, hydride ions, and ionic ligands for example hydrocarbon ligands such as cyclopentadienyls and substituted cyclopentadienyls, acetylacetonates and substituted acetylacetonates, or neutral ligands such as tertiary phosphines, ditertiary diphosphines, phosphites, olefins, carbon monoxide, or nitriles. These complexes of the invention may be mononuclear or polynuclear, neutral or ionic. They may contain a chiral ligand. Examples of complexes which can be used in the present invention are $RuH_4(PPh_3)_2$, $RhCl(PPh_3)_3$, $[Rh(norbornadiene)(PPh_3)_2]^+[PF_6]^-$, $[Rh(norbornadiene)(PPh_3)_2]^+[BF_4]^-$, $[Rh(norbornadiene)(PPh_3)_2]^+[ClO_4]^-$, $IrCl(PPh_3)_3$, $HRh(CO)(PPh_3)_3$, $(C_5H_5)RhCl_2$, $Rh(C_5Me_5)Cl_2(Ph_2PCH_2COPh)$, $IrCl(CO)(PPh_3)_2$, $[Rh(norbornadiene)(PPh_3)(Ph_2PCH_2COPh)]^-[PF_6]^-$, $[Rh(norbornadiene)(bisdiphenylarsinoethane)]^+[PF_6]^-$, $[Rh(norbornadiene)(bisdiphenylarsinoethane)]^+[PF_6]^-$, $[Rh(norbornadiene)(DIOP)]^-[PF_6]^-$, $[Ru(norbornadiene)(C_5Me_5)]^-[BF_4]^-$, $[(C_6Me_6)RuCl_2]_2$, $[(C_6H_6)RuCl_3Ru(C_6H_6)]PF_6$, and $[RhCl(cyclooctene)_2]$.

These complexes can be prepared remote from the reaction medium and introduced into it for reaction. They can also be formed in situ in the reaction medium, by introducing the components necessary for their formation. Other transition metal compounds can be used, such as inorganic salts (halides, for example chloride, bromide, iodide), oxides, hydroxides, or organic salts In general, the catalytic composition can contain an organic solvent such as an aromatic hydrocarbon or a hydrocarbon-containing compound. Preferably, the catalytic composition does not contain water.

The concentration of the compound (preferably a complex) of the transition metal in the molten salt is advantageously in the range 1 mmole of compound per litre of molten salt to 500 mmoles per litre, preferably in the range 2 mmoles per litre to 200 mmoles per litre, more preferably in the range 2 mmoles per litre to 100 mmoles per litre, most preferably in the range 2 mmoles per litre to 50 mmoles per litre The compounds in the composition of the invention can be mixed in any order at a temperature in the range $-20°$ C. to $+200°$ C., preferably in the range $-20°$ C. to $140°$ C., advantageously in the range $0°$ C. to $120°$ C., most preferably $0°$ to $80°$ C. or $0°$ C. to less than $50°$ C.

Examples of olefins which can be isomerised are 1-butene, 2-butene, 1-pentene, 2-pentene, 2-methyl-2-butene, 2-methyl-1-butene, 4-methyl-2-pentenes, 4-methyl-1-pentene, 2-methyl-1-pentene, 1-hexene, 2-hexenes, and 3-hexenes. More generally, the olefins can be linear branched or cyclic.

In the isomerisation process the olefin may be used pure or diluted by saturated or unsaturated hydrocarbons such as those found in cuts from various hydrocarbon refining, processes, for example butanes with butenes.

The isomerisation temperature is in the range $-10°$ C. to $200°$ C., advantageously less than $150°$ C., preferably in the range $=10°$ C. to less than $150°$ C.

Before bringing the olefin feed into contact with the catalytic composition, the composition is activated by hydrogen if necessary (not necessary in the case of hydrides, for example), at a temperature in the range $-10°$ C. to $200°$ C., advantageously less than $150°$ C., preferably between $+10°$ C. and less than $150°$ C. In catalyst compositions activated by hydrogen, hydrides are detected.

Advantageously, the isomerization reaction is preferably carried out in an inert atmosphere containing little or no hydrogen, the hydrogen/hydrocarbon molar ratio being preferably less than 0.01. Conversely, the isomerization can optionally be conducted under a total or partial pressure of hydrogen, for example, from subatmospheric to 20 MPa, especially between atmospheric pressure and 10 MPa. If isomerization is carried out under a hydrogen pressure, hydrogenation also occurs, except in the case where dichlorocuprate is the anion. In that case, hydrogenation remains at a very low level (see the following example). In the context of the present invention and claims, an isomerization process is a process wherein isomerization is the major reaction resulting in a product having a larger amount, by weight, of isomerizate than hydrogenate.

Catalytic isomerization of olefins can be carried out in a closed system, a batch system or in a continuous system using one or more reaction stages. At the reactor outlet, the organic phase containing the reaction products is advantageously separated by simple settling out of the polar catalytic phase containing the molten salt and the major portion of the catalyst. The polar phase which contains at least a portion of the catalyst is at least partially returned to the isomerization reactor, the other portion being treated to eliminate the remaining catalyst.

The following example illustrates the invention without in any way limiting its scope:

EXAMPLE 4 ml of butylmethylimidazolium dichlorocuprate and 43.2 mg (0.05 mmole) of $[Rh(norbornadiene)PPh_3)_2]+PF_6^-$ complex were introduced into a 50 ml capacity glass reactor which had been purged of air and moisture and placed under one atmosphere of hydrogen. The hydrogen pressure was taken to 0.1 MPa and the temperature taken to $30°$ C., for 10 minutes. The salt turned orange. After a return to atmospheric pressure, 2 ml of 1-pentene was injected and stirring was started in a hydrogen atmosphere. After 2 hours stirring, the mixture was allowed to settle; the supernatant hydrocarbon phase was extracted. 19% of the 1-pentene had been converted to 2-pentene, with no pentane formation. The reaction was repeated with the used salt, purged with hydrogen then put under an argon atmosphere. 91% of a new charge of 1-pentene was converted to 2-pentene at $25°$ C. for 17 hours, with no pentane formation.

The preceding example can be repeated with similar success by substituting the generically or specifically described reactants and/or operating conditions of this invention for those used in the preceding example.

The entire disclosure of all applications, patents and publications, cited above and below, and of corresponding French application 95/07329, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

In the following claims the catalyst composition is in the activated form—meaning that they contain hydrides. Also, any simultaneous hydrogenation constitutes a minor reaction as compared to the isomerization reaction. Conversely, in our concurrently filed cross referenced application Ser. No. 08/664,539, the hydrogenation constitutes the major reaction.

We claims:

1. A process for the double-bond isomerisation of olefins, comprising contacting an olefin in an isomerisation reactor under double-bond isomerizing condition with a catalytic composition comprising at least one compound of at least one transition metal from groups 8, 9 and 10 at least partially dissolved in at lest one molten salt selected from the group consisting of a quaternary ammonium and phosphonium salt, said salt being of the formula $Q^+A^-$ where $Q^+$ represent a quaternary ammonium or quaternary phosphonium cation and $A^-$ represents an anion selected from the group consisting of tetrafluoroborate, tetrachloroborate, hexafluorophosphate, hexafluoroantimonate, hexafluoroarsenate, dichlorocuprate, tetrachloroaluminate, trifluoromethylsulphonate, fluorosulphonate and trichlorozincate, resulting in products wherein any hydrogenated olefin constitutes a minor amount compared to double-bond isomerized olefin.

2. A process according to claim 1, in which the catalytic composition further comprises at least one anion selected from the group consisting of heptachloroaluminate, decachloroaluminate, trichlorocuprate and tetrachlorocuprate.

3. A process according to claim 1, in which the quaternary ammonium and/or phosphonium cation is selected from the group consisting of cations with general formula:

$R^1R^2R^3R^4N^+$
$R^1R^2N=CR^3R^{4+}$
$R^1R^2R^3R^4P^+$
$R^1R^2P=CR^3R^{4+}$

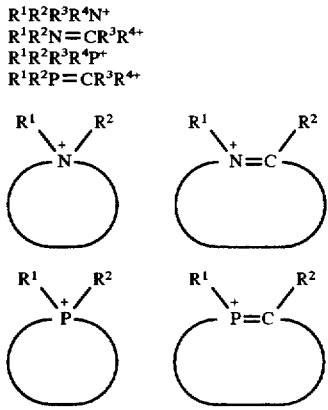

with the exception of the cation $NH_4^+$ and where $R^1$, $R^2$, $R^3$ and $R^4$, which may be identical or different, represent hydrogen, and hydrocarbon residues containing 1 to 12 carbon atoms, and in which the rings contain 4 to 10 atoms.

4. A process according to claim 1, in which the quaternary ammonium or phosphonium cation has one of the following general formulae:

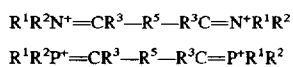

where $R^1$, $R^2$ and $R^3$, which may be identical or different, represent hydrogen or hydrocarbon residues containing 1 to 12 carbon atoms, and $R^5$ represents an alkylene or phenylene residue.

5. A process according to claim 1, in which the quaternary ammonium or phosphonium cation is selected from the group consisting of by N-butylpyridinium, N-ethylpyridinium, 3-butyl- 1-methylimidazolium, diethylpyrazolium, 3-ethyl-1-methylimidazolium, pyridinium, trimethylphenylammonium, 3-ethyl-1-methylimidazolium, and tetrabutylphosphonium.

6. A process according to claim 1, in which the quaternary ammonium or phosphonium salt is selected from the group consisting of N-butylpyridinium hexafluorophosphate, N-ethylpyridinium tetrafluoroborate, tetrabutylphosphonium tetrafluoroborate, 3-butyl-1-methylimidazolium hexafluoroantimonate, 3-butyl-1-methylimidazolium hexafluorophosphate, 3-butyl-1-methylimidazolium trifluoromethylsulphonate, pyridinium fluorosulphonate, trimethylphenylammonium hexafluorophosphate, 3-butyl-1-methylimidazolium tetrachloroaluminate, 3-butyl-1-methylimidazolium heptachloroaluminate, trimethylphenylammonium chloride, 3-ethly-1-methylimidazolium chloride, tetrabutylphosphonium bromide, N-butylpyridinium chloride, N-ethylpyridinium bromide, 3-butyl-1-methylimidazolium chloride, diethylpyrazolium chloride, and pyridinium hydrochloride.

7. A process according to claim 1, in which the transition metal is selected from the group consisting of ruthenium, rhodium and iridium.

8. A process according to claim 1, in which the transition metal compound is a transition metal complex.

9. A process according to claim 1, in which the metal is bonded to neutral or ionic ligands.

10. A process according to claim 8, in which the complex is selected from the group consisting of $RuH_4(PPh_3)_2$, $RhCl(PPh_3)_3$, $[Rh(norbornadiene)(PPh_3)_2]^+[PF_6]^-$, $IrCl(PPh_3)_3$, $HRh(CO)(PPh_3)_3$, $(C_5H_5)RhCl_2$, $IrCl(CO)(PPh_3)_2$, $[Rh(norbornadiene) (PPh_3)(Ph_2PCH_2COPh)]^-[PF_6]^{31}$, $[Rh(norbornadiene) (bisdiphenyphosphinoethane)]^+[PF_6]^{31}$, $[Rh(norbornadiene) (bisdiphenylarsinoethane)]^+[PF_6]^-$, $[Ru(norbornadiene)(C_5Me_5)]^+[BF_4]^-$, $[(C_6Me_6)RuCl_2]_2$, and $[(C_6H_6)RuCl_3(C_6H_6)]^+PF_6^-$.

11. A process according to claim 1, in which the concentration of the compound of transition metal from groups 8 to 10 is 1 to 500 mmoles per litre with respect to the ammonium and/or phosphonium salt.

12. A process according to claim 1, in which the catalytic composition comprises an organic solvent.

13. A process according to claim 1, in which said olefin is at least one member selected from the group consisting of 1-butene, 2-butene, 1-pentene, 2-pentene, 2-methyl-2-butene, 2-methyl-1-butene, a 4-methyl-2-pentene, 4-methyl-1-pentene, 2-methyl-1-pentene, 1-hexene, a 2-hexene, and a 3-hexene.

14. A process according to claim 1, further comprising withdrawing an effluent from the reactor, said effluent having a hydrocarbon phase and a polar phase, said polar phase containing at least a portion of the catalyst, separating said polar phase from the hydrocarbon phase, and recycling said polar phase at least in part to the isomerisation reactor.

15. A process according to claim 1, carried out at −10° C. to 200° C., at a pressure in the range 0.1 MPa to 20 MPa.

16. A process according to claim 1, wherein said anion is dichlorocuprate.

17. A process according to claim 1, wherein the isomerisation is conducted under a substantially inert atmosphere, containing a hydrogen/hydrocarbon molar ratio of less than 0.01:1.

18. A process according to claim 1, wherein said salt has a melting point of not more than 80° C.

19. A process according to claim 1, wherein said salt has a melting point less than 50° C.

20. A process according to claim 1, wherein the isomerisation is conducted at 25–30° C.

21. A process according to claim 1, wherein the olefin is a mono-olefin.

* * * * *